United States Patent
Vanhoorne et al.

(10) Patent No.: US 8,362,182 B2
(45) Date of Patent: *Jan. 29, 2013

(54) PROCESS FOR PRODUCING CATION EXCHANGERS

(75) Inventors: Pierre Vanhoorne, Monheim (DE); Hans-Jurgen Wedemeyer, Leverkusen (DE)

(73) Assignee: LANXESS Deutschland GmbH, Leverkusen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/482,272

(22) Filed: May 29, 2012

(65) Prior Publication Data

US 2012/0238649 A1 Sep. 20, 2012

Related U.S. Application Data

(62) Division of application No. 13/268,122, filed on Oct. 7, 2011, now Pat. No. 8,207,284, which is a division of application No. 12/334,570, filed on Dec. 15, 2008, now abandoned.

(30) Foreign Application Priority Data

Dec. 18, 2007 (DE) .......... 10 2007 060 790

(51) Int. Cl.
*C08F 12/02* (2006.01)
*C08F 16/12* (2006.01)
*C08F 118/02* (2006.01)
*C08F 4/44* (2006.01)
*B29B 7/76* (2006.01)
*C08J 5/20* (2006.01)
*C02F 1/42* (2006.01)

(52) U.S. Cl. ........ 526/346; 526/332; 526/319; 536/127; 521/133; 521/25; 210/681

(58) Field of Classification Search ............ 526/346, 526/332, 319; 536/127; 521/133, 25; 210/681
See application file for complete search history.

(56) References Cited

U.S. PATENT DOCUMENTS

2008/0096987 A1* 4/2008 Podszun et al. .......... 521/25

OTHER PUBLICATIONS

Pure Appl. Chem., vol. 76, No. 4, p. 889-906, 2004.*

\* cited by examiner

*Primary Examiner* — William Cheung
(74) *Attorney, Agent, or Firm* — Nicanor A. Kohncke

(57) ABSTRACT

Strongly acidic cation exchangers with high mechanical, osmotic and oxidation stability can be prepared by sulfonating bead polymers formed from one or more vinylaromatic monomer(s), one or more crosslinker(s) and from 0.2 to 20% by weight of one or more vinyl ethers and/or vinyl esters.

10 Claims, No Drawings

PROCESS FOR PRODUCING CATION EXCHANGERS

This application is a divisional of U.S. patent application Ser. No. 13/268,122 filed Oct. 7, 2011, U.S. Pat. No. 8,207,284, which is a divisional of U.S. patent application Ser. No. 12/334,570 filed Dec. 15, 2008, now abandoned, entitled "PROCESS FOR PRODUCING CATION EXCHANGERS", which claims priority to German patent application No. 10 2007 060 0790.5 filed Dec. 18, 2007, the contents of which are hereby incorporated by reference in their entirety.

The invention relates to a process for producing strongly acidic cation exchangers with high mechanical, osmotic and oxidation stability by sulfonating bead polymers formed from one or more vinylaromatic monomer(s), one or more crosslinker(s) and one or more ether(s) and/or ester(s) of vinyl alcohol.

BACKGROUND OF THE INVENTION

Strongly acidic cation exchangers can be obtained by functionalizing crosslinked styrene bead polymers. The functionalization generates covalently bonded sulfonic acid groups through reaction of aromatic units of the polymer skeleton with a sulfonating agent, for example sulfuric acid.

One problem with the known strongly acidic cation exchangers is that of their stability under stress, which is not always sufficient. For instance, cation exchanger beads can break up as a result of mechanical or osmotic forces. For all applications of cation exchangers, the exchangers present in bead form must maintain their habit and must not be degraded partly or even entirely during the application or break up into fragments. Fragments and bead polymer splinters can get into the solutions to be purified during the purification and contaminate them themselves. Moreover, the presence of damaged bead polymers is unfavorable for the functioning of the cation exchangers themselves which are used in column processes. Splinters lead to an elevated pressure drop of the column system and hence reduce the throughput of the liquid to be purified through the column.

A further problem of the known strongly acidic cation exchangers is their tendency to release sulfonated, water-soluble fragments from water in use as a result of the action of a wide variety of different oxidizing agents dissolved in water (atmospheric oxygen, hydrogen peroxide, vanadyl salts, chromates). This phenomenon, known in general to those skilled in the art by the term "leaching" leads to the enrichment of sulfonated organic constituents in the water to be treated, which can lead to various problems in the downstream systems which are reliant on the supply of fully demineralized water. For example, the water-soluble fragments lead, for example, to corrosion problems in the cooling circuit of power plants, to defects in the microchips produced in the electronics industry, to the failure of the system owing to excessively high electrical conductivity of the water in eroding machines.

There has been no lack of attempts to provide strongly acidic cation exchangers which have an improved mechanical stability, osmotic stability and/or an improved oxidation stability.

For instance, the mechanical and osmotic stability of strongly acidic cation exchangers can be increased via two-stage structure of the bead polymers, in a so-called seed-feed process. Such processes are described, for example, in EP 0 101 943 A2, EP-A 1 000 659 and DE-A 10 122 896. The cation exchangers produced in two stages exhibit an outstanding mechanical stability, but release significantly more sulfonated degradation products to the treated water than the resins produced in one stage.

The incorporation of small amounts of acrylate monomers into the styrene-divinylbenzene copolymer also leads to an increased mechanical stability, as described in U.S. Pat. No. 4,500,652 and DE-A 3 230 559. However, the presence of acrylic acid units in the polymer structure leads to a higher oxidation susceptibility of the resins.

Bachmann et al. describe in EP-A 868 444, a process for producing mechanically and osmotically stable cation exchangers by sulfonating without addition of chlorinated swelling agents at temperatures between 125 and 180° C. However, dispensing with the chlorinated swelling agent in the sulfonation does not improve the oxidation stability of the resins.

The oxidation stability of the strongly acidic cation exchangers can be increased by adding antioxidants, as described, for example, in EP-A 0 366 258. These antioxidants are washed slowly out of the resin, which leads to the release of organic constituents to the water treated. Furthermore, they are spent after a relatively short time in use. Thereafter, the resin treated with antioxidants exhibits the same oxidation sensitivity as a conventional strongly acidic cation exchanger.

The oxidation stability of the strongly acidic cation exchangers can also be improved by increasing the crosslinking density of the bead polymer. However, the incorporation of major amounts of crosslinker makes the polymers more brittle, which leads to a significant reduction in the mechanical stability of the beads. Moreover, the kinetics of the cation exchange decrease significantly with increasing crosslinking density, which leads to insufficient absorption capacities in many applications.

There is thus still a need for cation exchangers with rapid exchange kinetics, high mechanical and osmotic stability, and simultaneously high oxidation stability.

The problem addressed by the present invention is therefore that of providing a simple, robust and economically viable process for producing cation exchangers with rapid exchange kinetics, high mechanical and osmotic stability, and high oxidation stability.

SUMMARY OF THE INVENTION

The solution to the problem and hence the subject-matter of the present invention is a process for producing strongly acidic cation exchangers by sulfonating crosslinked bead polymers formed from vinylaromatic monomers, wherein the bead polymers comprise from 0.2 to 20% by weight of vinyl ethers and/or vinyl esters as comonomer(s).

Surprisingly, cation exchangers which are obtained by the process according to the invention have a significantly higher oxidation stability as compared with the prior art, coupled with equal or higher mechanical and osmotic stability. It has additionally been found that, surprisingly, the improvement in the oxidation stability of the strongly acidic cation exchangers obtained from the inventive bead polymers is attributable solely to the incorporation of the comonomer in the bead polymer, irrespective of in what manner and at what time the comonomer is added and polymerized in the course of formation of the bead polymer.

For clarification, it should be noted that the scope of the invention encompasses all definitions and parameters cited below, in general or within areas of preference, in all combinations.

Crosslinked bead polymers suitable in accordance with the invention are copolymers of at least one monoethylenically unsaturated aromatic monomer, at least one crosslinker and at least one vinyl ether or vinyl ester.

The monoethylenically unsaturated aromatic (=vinylaromatic) monomers used are preferably styrene, α-methylstyrene, vinyltoluene, ethylstyrene, t-butylstyrene, chlorostyrene, bromostyrene, chloromethylstyrene or vinylnaphthalene. Also very suitable are mixtures of these monomers. Particular preference is given to styrene and vinyltoluene.

Crosslinkers are added to the monomers. Crosslinkers are generally polyethylenically unsaturated compounds, preferably divinylbenzene, divinyltoluene, trivinylbenzene, octadiene or triallyl cyanurate. The vinylaromatic crosslinkers are more preferably divinylbenzene and trivinylbenzene. Very particular preference is given to divinylbenzene. To prepare the bead polymers, it is possible to use technical-grade qualities of divinylbenzene which, as well as the isomers of divinylbenzene, comprise customary by-products such as ethylvinylbenzene. According to the invention, technical-grade qualities with divinylbenzene contents of from 55 to 85% by weight are particularly suitable.

The crosslinkers can be used alone or as a mixture of different crosslinkers. The total amount of crosslinkers for use is generally from 0.1 to 80% by weight, preferably from 0.5 to 60% by weight, more preferably from 1 to 40% by weight, based on the sum of the ethylenically unsaturated compounds.

The comonomer(s) used are vinyl ethers and/or vinyl esters.

In the context of the present invention, vinyl ethers are understood to mean the ethers of vinyl alcohol and of isopropenyl alcohol. Vinyl ethers in the context of the present invention may contain one or more vinyl or isopropenyl alcohol units. Preference is given to alkyl and hydroxyalkyl ethers having from 1 to 18 carbon atoms, and ethers with condensation products of ethylene glycol. Particular preference is given to methyl vinyl ether, ethyl vinyl ether, ethylene glycol monovinyl ether, ethylene glycol divinyl ether, diethylene glycol monovinyl ether, diethylene glycol divinyl ether, butanediol monovinyl ether, butanediol divinyl ether, methyl isopropenyl ether or ethyl isopropenyl ether. Very particular preference is given to using ethylene glycol divinyl ether, diethylene glycol divinyl ether and butanediol divinyl ether.

In the context of the present invention, vinyl esters are understood to mean the esters of vinyl alcohol and of isopropenyl alcohol. Vinyl esters in the context of the present invention may contain one or more vinyl or isopropenyl alcohol units. Preference is given to esters of carboxylic acids having from 1 to 18 carbon atoms. Particular preference is given to using vinyl formate, vinyl acetate, vinyl propionate, vinyl butyrate, vinyl valerate, vinyl hexanoate, vinyl octoate, vinyl decanoate, vinyl laurate, vinyl myristate, vinyl oleate, vinyl palmitate, vinyl benzoate, divinyl phthalate or isopropenyl acetate. Very particular preference is given to using vinyl acetate and isopropenyl acetate.

It is also possible to use mixtures of vinyl ethers, mixtures of vinyl esters or mixtures of vinyl ethers with vinyl esters.

The comonomer is used in amounts of from 0.2 to 20% by weight, based on the sum of vinylaromatic monomers and crosslinkers. Preference is given to using amounts of from 0.5 to 15% by weight, more preferably from 1 to 10% by weight. When mixtures of vinyl ethers and/or vinyl esters are used, the amounts are based on the sum of all comonomers.

In a preferred embodiment of the present invention, the comonomer can be added to the monomer mixture before the polymerization sets in. However, it can also be metered in the course of the polymerization, preferably at a polymerization conversion between 10 and 90%, more preferably between 15 and 80%.

In a further preferred embodiment of the present invention, the comonomer is added to the aqueous phase in the course of the polymerization together with a water-soluble initiator. Suitable water-soluble initiators in this preferred embodiment are compounds which form free radicals when the temperature is increased. Preference is given to peroxodisulfates, particular preference to potassium peroxodisulfate, sodium peroxodisulfate and ammonium peroxodisulfate, water-soluble azo compounds, more preferably 2,2'-azobis(2-amidinopropane) hydrochloride, 2,2'-azobis[N-(2-carboxyethyl)-2-methylpropionamidine]tetrahydrate, 2,2'-azobis[N,N'-dimethyleneisobu tyramidine], 4,4'-azobis(4-cyanovaleric acid), and also hydroperoxides, more preferably t-butyl hydroperoxide and cumyl hydroperoxide.

However, the comonomer can also be added after the polymerization of the bead polymer has ended and can be polymerized in a separate polymerization step.

In a preferred embodiment of the present invention, it is also possible to add pore formers, known as porogens, to the monomers. The porogens serve for the formation of a pore structure in the nonfunctional bead polymer. The porogens used are preferably organic diluents. Particular preference is given to using those organic diluents which dissolve in water to an extent of less than 10% by weight, preferably less than 1% by weight. Especially suitable porogens are toluene, ethylbenzene, xylene, cyclohexane, octane, isooctane, decane, dodecane, isododecane, methyl isobutyl ketone, ethyl acetate, butyl acetate, dibutyl phthalate, n-butanol, 4-methyl-2-pentanol or n-octanol. Very particular preference is given to toluene, cyclohexane, isooctane, isododecane, 4-methyl-2-pentanol or methyl isobutyl ketone. The porogens used may also be uncrosslinked, linear or branched polymers, for example polystyrene and polymethyl methacrylate. Also suitable are mixtures of different porogens.

The porogen is used typically in amounts of from 10 to 70% by weight, preferably from 25 to 65% by weight, based in each case on the sum of the ethylenically unsaturated compounds.

To prepare the crosslinked bead polymers, the abovementioned monomers, in a further preferred embodiment of the present invention, are polymerized in the presence of a dispersing assistant using an initiator in aqueous suspension.

The dispersing assistants used are preferably natural and synthetic water-soluble polymers. Particular preference is given to using gelatin, starch, cellulose derivatives, polyvinyl alcohol, polyvinylpyrrolidone, polyacrylic acid, polymethacrylic acid or copolymers of (meth)acrylic acid and (meth)acrylic esters. Very particular preference is given to using gelatins or cellulose derivatives, especially cellulose esters and cellulose ethers, such as carboxymethylcellulose, methylcellulose, hydroxyethylcellulose or methylhydroxyethylcellulose. The amount of the dispersing assistants used is generally from 0.05 to 1%, preferably from 0.1 to 0.5%, based on the water phase.

In a further preferred embodiment of the present invention, initiators are used in the monomer mixture. In the present invention, the monomer mixture refers to the mixture of vinylaromatic monomers, crosslinker(s), comonomer(s) and if appropriate porogen(s). Suitable initiators are compounds which form free radicals when the temperature is increased and dissolve in the monomer mixture. Preference is given to peroxy compounds, particular preference to dibenzoyl peroxide, dilauryl peroxide, bis(p-chlorobenzoyl) peroxide, dicyclohexyl peroxydicarbonate or tert-amylperoxy-2-ethylhexane, and also to azo compounds, particular preference to 2,2'-azobis(isobutyronitrile) or 2,2'-azobis(2-methylisobutyronitrile), or else aliphatic peroxy esters, preferably tert-butyl peroxyacetate, tert-butyl peroxyisobutyrate, tert-butyl peroxypivalate, tert-butyl peroxyoctoate, tert-butyl peroxy-2-ethylhexanoate, tert-butyl peroxyneodecanoate, tert-amyl peroxypivalate, tert-amyl peroxyoctoate, tert-amyl peroxy-2-ethylhexanoate, tert-amyl peroxyneodecanoate, 2,5-bis (2-ethylhexanoylperoxy)-2,5-dimethylhexane, 2,5-dipivaloyl-2,5-dimethylhexane, 2,5-bis (2-neodecanoylperoxy)-2,5-dimethylhexane, di-tert-butyl peroxyazelate or di-tert-amyl peroxyazelate.

The initiators which are soluble in the monomer mixture are employed generally in amounts of from 0.05 to 6.0% by weight, preferably from 0.1 to 5.0% by weight, more preferably from 0.2 to 2% by weight, based on the sum of the ethylenically unsaturated compounds.

The water phase may comprise a buffer system which adjusts the pH of the water phase to a value between 12 and 3, preferably between 10 and 4. Particularly suitable buffer systems contain phosphate, acetate, citrate or borate salts.

It may be advantageous to use an inhibitor dissolved in the aqueous phase. Useful inhibitors include both inorganic and organic substances. Examples of inorganic inhibitors are nitrogen compounds such as hydroxylamine, hydrazine, sodium nitrite or potassium nitrite. Examples of organic inhibitors are phenolic compounds such as hydroquinone, hydroquinone monomethyl ether, resorcinol, pyrocatechol, tert-butylpyrocatechol, condensation products of phenols with aldehydes. Further organic inhibitors are nitrogen-containing compounds, for example diethylhydroxylamine and isopropylhydroxylamine. Resorcinol is preferred as an inhibitor. The concentration of the inhibitor is 5-1000 ppm, preferably 10-500 ppm, more preferably 20-250 ppm, based on the aqueous phase.

The organic phase can be dispersed into the aqueous phase as droplets by stirring or by jetting. The organic phase is understood to mean the mixture of monomer(s) and crosslinker(s), and also, if appropriate, additionally porogen(s) and/or initiator(s). In conventional dispersion polymerization, the organic droplets are generated by stirring. On the 4 liter scale, stirrer speeds of from 250 to 400 rpm are typically used. When the droplets are generated by jetting, it is advisable to maintain the homogeneous droplet diameter by encapsulating the organic droplets. Processes for microencapsulating jetted organic droplets are described, for example, in EP 0 046 535, whose contents in relation to microencapsulation are encompassed by the present application.

The mean particle size of the unencapsulated or encapsulated monomer droplets is 10-1000 µm, preferably 100-1000 µm.

The ratio of the organic phase to the aqueous phase is generally from 1:20 to 1:0.6, preferably from 1:10 to 1:1, more preferably from 1:5 to 1:1.2.

However, the organic phase can also, according to EP-A 0 617 714 whose teaching is encompassed by the present application, be added in the so-called seed-feed process to a suspension of seed polymers which absorb the organic phase. The mean particle size of the seed polymers swollen with the organic phase is 5-1200 µm, preferably 20-1000 µm. The ratio of the sum of organic phase+seed polymer relative to the aqueous phase is generally 1:20 to 1:0.6, preferably 1:10 to 1:1, more preferably 1:5 to 1:1.2.

The polymerization of the monomers and comonomers is performed at elevated temperature. The polymerization temperature is guided by the decomposition temperature of the initiator and is typically in the range from 50 to 150° C., preferably from 60 to 130° C. The polymerization time is from 30 minutes to 24 hours, preferably from 2 to 15 hours.

At the end of the polymerization, the crosslinked bead polymers are removed from the aqueous phase, preferably on a suction filter, and optionally dried.

The crosslinked bead polymers are converted to cation exchangers by sulfonation. Useful sulfonating agents include sulfuric acid, chlorosulfonic acid and sulfur trioxide. Preference is given to using sulfuric acid.

The sulfuric acid is used preferably in a concentration of from 80 to 120%, more preferably from 85 to 105%, most preferably from 88 to 99%. For the sulfuric acid, in the present invention, concentration figures more than 100% mean solutions of sulfur trioxide ($SO_3$) in 100% sulfuric acid. For instance, a sulfuric acid concentration of 120% is understood to mean a 20% solution of $SO_3$ in 100% sulfuric acid.

It is advantageous to establish the necessary acid concentration by mixing sulfuric acid of a relatively high concentration and of a relatively low concentration, in which case the sulfuric acid with a relatively low concentration used may be recovered sulfuric acid from earlier sulfonation reactions. The mixing of the sulfuric acid can be effected in the sulfonation reactor in the presence of the bead polymer to be sulfonated, such that the resulting heat of mixing leads to a temperature increase in the reaction mixture.

The ratio of sulfuric acid to bead polymer is from 2.0 to 6 ml/g, preferably from 2.5 to 5 ml/g, more preferably from 2.6 to 4.2 ml/g.

If desired, a swelling agent, preferably chlorobenzene, dichloroethane, dichloropropane or methylene chloride, can be employed in the sulfonation. The swelling agent is used preferably in amounts of from 0.1 to 1 ml per gram of dry bead polymer, more preferably from 0.2 to 0.5 ml per gram of dry bead polymer. The swelling agent is preferably added to the bead polymer initially charged in sulfuric acid before the onset of the sulfonation reaction.

The temperature in the sulfonation is generally 50-200° C., preferably 80-160° C., more preferably 90-140° C. It may be advantageous to employ a temperature program in the sulfonation, in which the sulfonation is commenced at a first temperature in a first reaction step and continued at a higher temperature in a second reaction step.

In the sulfonation, the reaction mixture is stirred. It is possible to use different stirrer types, such as paddle stirrers, anchor stirrers, gate stirrers or turbine stirrers.

The duration of the sulfonation reaction is generally several hours, preferably between 1 and 24 h, more preferably between 2 and 16 h, most preferably between 3 and 12 h.

After the sulfonation, the reaction mixture composed of sulfonation product and residual acid is cooled to room temperature and diluted first with sulfuric acids of decreasing concentrations and then with water.

If desired, the cation exchanger obtained in accordance with the invention can be treated in the H form, for purification, with deionized water at temperatures of 70-180° C., preferably of 105-130° C.

For many applications, it is favorable to convert the cationic exchanger from the acidic form to the sodium form. This conversion is effected with sodium hydroxide solution of a concentration of 2-60% by weight, preferably 4-10% by weight, or with aqueous sodium chloride solutions which are 1-25% by weight, preferably 4-10% by weight, in sodium chloride.

After the conversion, the cation exchangers can be purified further by treating with deionized water or aqueous salt solutions, for example with sodium chloride or sodium sulfate solutions. It has been found that the treatment at 70-150° C., preferably 120-135° C., is particularly effective and does not bring about any reduction in the capacity of the cation exchanger.

The inventive, strongly acidic cation exchangers may contain pores. Porous inventive strongly acidic cation exchangers may be microporous, mesoporous and/or macroporous. For the definition of the terms "gel-form", "porous", "microporous", "mesoporous" and "macroporous" for polymers, reference is made to Pure Appl. Chem., Vol. 76, No. 4, p. 889-906, 2004 (IUPAC recommendations 2003), more particularly to p. 900 §3.9 and p. 902-903 §3.23.

The inventive, strongly acidic cation exchangers have a mean particle size D between 30 µm and 1000 µm, preferably between 100 and 800 µm. To determine the mean particle size and the particle size distribution, customary methods, such as screen analysis or image analysis, are suitable. The mean particle size D is understood in the context of the present invention to mean 50% value (Ø(50)) of the volume distribution. The 50% value (Ø(50)) of the volume distribution indicates the diameter which is above that of 50% by volume of the particles.

In a preferred embodiment of the present invention, monodisperse strongly acidic cation exchangers are produced. Monodisperse particle size distributions in the context of the present invention have a proportion by volume of particles between 0.9 D and 1.1 D of at least 75% by volume, preferably at least 85% by volume, more preferably at least 90% by volume.

The present invention also relates to a process for producing strongly acidic cation exchangers, characterized in that:
a) monodisperse or heterodisperse bead polymers are prepared from vinylaromatic monomers, crosslinkers and from 0.2 to 20% by weight of vinyl ethers and/or vinyl esters by suspension polymerization and
a) these bead polymers are converted to strongly acidic cation exchangers by the action of sulfuric acid, sulfur trioxide and/or chlorosulfonic acid.

The strongly acidic cation exchangers obtained by the process according to the invention are notable for a particularly high mechanical stability, osmotic stability and oxidation stability. Even after prolonged use and multiple regeneration, they exhibit barely any defects in the ion exchanger spheres.

For the inventive strongly acidic cation exchangers, there is a multitude of different applications. For example, they can be used in drinking water treatment, in the production of power plant water and ultrapure water (needed in microchip production for the computer industry), for chromatographic separation of glucose and fructose and as catalysts for various chemical reactions (for example bisphenol A preparation from phenol and acetone).

It will be understood that the specification and examples are illustrative but not limitative of the present invention and that other embodiments within the spirit and scope of the invention will suggest themselves to those skilled in the art.

Analysis Methods:
Volume-based total capacity 20 ml of exchanger are shaken in under demineralized water on a tamping volumeter. In a 200 ml beaker, these 20 ml of exchanger, 5 g of NaCl p.a. and 50 ml of sodium hydroxide solution c(NaOH)=1 mol/l are combined and titrated with hydrochloric acid c(HCl)=1.0 mol/l down to pH=4.3.

The total capacity of the cation exchanger is calculated as follows:

$$TC = \frac{\text{Consumption of HCl } c(\text{HCl}) = 1.0 \text{ mol/l}}{20}$$

Original Stability: Number of Perfect Beads after Production 100 beads are viewed under a microscope. The number of beads which bear cracks or exhibit splintering-off is determined. The number of perfect beads is calculated from the difference between the number of damaged beads and 100.

Determination of the Osmotic Stability of Cation Exchangers through Swelling stability In the swelling stability test, the exchangers are treated in a filter tube alternately with hydrochloric acid w(HCl)=6% and sodium hydroxide solution w(NaOH)=4%. There is intermediate treatment in each case with demineralized water.

For the test, 25 ml of exchanger shaken in under demineralized water are installed into a filter tube.

Then the resin is rinsed back with demineralized water for 5 minutes. The rate of back-rinsing is regulated such that the resin is distributed over the entire filter tube length.

After the back-rinsing has ended, 40 working operations are carried out. One working operation comprises 4 cycles of 10 minutes each of loading and regeneration and 2×5 minutes each of back-rinsing. Acid and alkali run through the exchangers at 500 ml per cycle through capillaries.

After the test has ended, the exchanger is flushed out of the filter tube, and the water is sucked in with the screen tube and mixed thoroughly.

The exchanger is then counted under the microscope for the percentage of whole beads, of cracked beads and splinters as in the determination of the original stability.

Determination of the Oxidation Stability of Cation Exchangers by Reddening Test 750 ml of resin are shaken in and washed in cocurrent with UPW water at a rate of 15 l/h for 4 hours. UPW water is defined as water having a conductivity of <17.8 MOhm cm and a content of organic material (TOC) <2.00 ppb. After the washing, the 750 ml of resin are subjected to suction on a glass suction filter for 5 minutes. For the conductivity of UPW, see also 1998 Semiconductor Pure Water and Chemicals Conference, Mar. 2-5, 1998, Advances in Resistivity Instrumentation for UPW Systems of the Future, Anthony C. Bevilacqua under: http://www.gatewayequipment.com/whitepapers/resistivity_instru_futureUPWsystems.pdf.

50 g of the washed and suctioned cation exchanger are transferred into a glass bottle. The closed glass bottle is stored in daylight at room temperature for 4 weeks. At the end of the storage time, the resin is admixed with 100 g of UPW water and shaken at 100 rpm for 10 minutes. Subsequently, the sample is filtered off and the eluate is tested by the following methods: pH, absorbance at 225 nm (1 cm cuvette) and visual assessment of reddening, the mark 0 indicating a completely colorless eluate and the mark 4 a deep red eluate.

Demineralized water in the context of the present invention is characterized in that it possesses a conductivity of from 0.1 to 10 µS, the content of dissolved or undissolved metal ions being not greater than 1 ppm, preferably not greater than 0.5 ppm for Fe, Co, Ni, Mo, Cr, Cu as individual components, and being not greater than 10 ppm, preferably not greater than 1 ppm, for the total of the metals mentioned.

EXAMPLES

Example 1

Preparation of a Monodisperse Seed Bead Polymer based on Styrene, Divinylbenzene and Ethylstyrene A 4 l glass reactor was initially charged with 1020 g of demineralized water, and a solution of 3.2 g of gelatin, 4.8 g of disodium hydrogenphosphate dodecahydrate and 0.24 g of resorcinol in 86 g of demineralized water was added and mixed. The temperature of the mixture was adjusted to 25° C. With stirring, 1182 g of microencapsulated monomer droplets which had been obtained by jetting and had a narrow particle size distribution, containing 4.5% by weight of divinylbenzene, 1.12% by weight of ethylstyrene, 0.36% by weight of tert-butyl peroxy-2-ethylhexanoate and 94.02% by weight of styrene, were added with stirring, the microcapsules having consisted of a formaldehyde-hardened complex coacervate of gelatin and a copolymer of acrylamide and acrylic acid, and 1182 g of aqueous phase with a pH of 12 were added.

The mixture was polymerized to completion with stirring by increasing the temperature according to a temperature program beginning at 25° C. and ending at 95° C. The mixture was cooled, washed over a 315 µm screen and then dried at 80° C. under reduced pressure. 1152 g of a seed bead polymer having a mean particle size of 365 µm, and narrow particle size distribution and a smooth surface were obtained.

Comparative Example 1

(Noninventive)

C1a) Preparation of a Bead Polymer without Comonomer

In a 4 l stirred reactor with gate stirrer, cooler, temperature sensor and thermostat and temperature recorder, an aqueous initial charge composed of 1443 g of deionized water and 5.88 g of disodium hydrogenphosphate dodecahydrate was obtained. To this initial charge were added, with stirring at 200 rpm, 864.9 g of seed polymer from example 1.

Within 30 min, a mixture of 625.7 g of styrene, 109.5 g of divinylbenzene (81.3%) and 5.88 g of dibenzoyl peroxide was added. To remove atmospheric oxygen, the mixture was then sparged with nitrogen for 15 minutes. Subsequently, the reactor contents were brought to 30° C. within 30 minutes and kept at this temperature for a further 30 minutes. Then a solution of 3.2 g of methylhydroxyethylcellulose dissolved in 157 g of water was added and the mixture was stirred at 30° C. for another hour. The mixture was heated to 62° C. for 16 hours and then to 95° C. for 2 hours. After cooling, the mixture was washed over a 315 µm screen and dried. 1465 g of a monodisperse bead polymer having a mean particle size of 448 µm were obtained.

C1b) Production of a Cation Exchanger

A 4 l stirred reactor with gate stirrer, temperature sensor, distillation system and thermostat and temperature recorder was initially charged with 741 ml of 87.8% by weight sulfuric acid at room temperature. Within 30 minutes, 350 g of bead polymer from C1a) and 88 ml of 1,2-dichloroethane were introduced with stirring. The reactor contents were stirred at 40° C. for 30 minutes. Subsequently, 159 ml of oleum (65% by weight SO$_3$ in 100% by weight sulfuric acid) were added within one hour without the reactor temperature exceeding 90° C. Then the mixture was heated to 115° C. and stirred at 115° C. for 5 hours, in the course of which the 1,2-dichloroethane was removed by means of a distillation system. The reaction mixture was subsequently brought to 140° C. and stirred at 140° C. for 3 hours. After cooling, the suspension was transferred to a glass column. Sulfuric acid of decreasing concentration, beginning with 90% by weight and ending with pure water, was applied to the column from the top. 1460 ml of monodisperse cation exchanger in the H form with a total capacity, based on the H form, of 2.08 eq/l were obtained.

Comparative Example 2

(Noninventive)

C2a) Preparation of a Bead Polymer without Comonomer

In a 4 l stirred reactor with gate stirrer, condenser, temperature sensor and thermostat and temperature recorder, an aqueous initial charge composed of 1342 g of deionized water, 5.3 g of boric acid and 2.97 g of 50% by weight sodium hydroxide solution was obtained. To this initial charge were added, with stirring at 200 rpm, 802.4 g of seed polymer prepared according to example 1.

Within 30 min, a mixture of 687.7 g of styrene, 114.7 g of divinylbenzene (80.5%) and 2.57 g of tert-butyl peroxy-2-ethylhexanoate was added. To remove atmospheric oxygen, the mixture was then sparged with nitrogen for 15 minutes. Subsequently, the reactor contents were brought to 30° C. within 30 minutes and kept at this temperature for a further 2 hours. A solution of 3.2 g of methylhydroxyethylcellulose dissolved in 157 g of water was then added and the mixture was stirred at 30° C. for another hour. The mixture was heated to 65° C. for 11 hours and then to 95° C. for 2 hours. After cooling, the mixture was washed over a 315 µm screen and dried. 1544 g of a monodisperse bead polymer having a mean particle size of 460 µm were obtained.

C2b) Production of a cation exchanger

A 4 l stirred reactor with gate stirrer, temperature sensor, distillation system and thermostat and temperature recorder was initially charged with 1400 ml of 98% by weight sulfuric acid and heated to 100° C. Within 30 minutes, 350 g of bead polymer from C2a) were introduced in 10 portions with stirring. Subsequently, the mixture was stirred at 100° C. for 30 minutes and at 115° C. for 5 hours. After cooling, the suspension was transferred into a glass column. Sulfuric acid of decreasing concentration, beginning with 90% by weight and ending with pure water, was applied to the column from the top.

1440 ml of monodisperse cation exchanger in the H form with a total capacity, based on the H form, of 2.2 eq/l were obtained.

Comparative Example 3

(Noninventive)

C3a) Preparation of a Bead Polymer with Acrylonitrile according to DE-A 10 122 896

The procedure was as in example C2a), except that 4.71 g of boric acid and 2.64 g of 50% by weight sodium hydroxide solution were used in the initial charge. To this were added 891.5 g of seed polymer, prepared as in example 1, and a mixture of 560.3 g of styrene, 88.7 g of divinylbenzene (81.3%), 64.2 g of acrylonitrile and 2.28 g of tert-butyl peroxy-2-ethylhexanoate. The mixture was heated to 61° C. for 11 hours and then to 130° C. for 2 hours.

1505 g of a monodisperse bead polymer having a mean particle size of 442 µm were obtained.

C3b) Production of a Cation Exchanger

The procedure was as in example C2b), except that 2800 ml of 98% by weight sulfuric acid were initially charged and 700 g of bead polymer from C3a) were introduced and the mixture was stirred at 105° C. for 5 hours.

3000 ml of monodisperse cationic exchanger in the H form with a total capacity, based on the H form, of 1.92 eq/l were obtained.

Example 2

(Inventive)

2a) Preparation of a Bead Polymer with Diethylene Glycol Divinyl Ether

In a 4 l stirred reactor with gate stirrer, condenser, temperature sensor and thermostat and temperature recorder, an aqueous initial charge composed of 1443 g of deionized water and 5.88 g of disodium hydrogenphosphate dodecahydrate was obtained. To this initial charge were added, with stirring at 200 rpm, 864.9 g of seed polymer prepared as in example 1.

Within 30 min, a mixture of 625.7 g of styrene, 109.5 g of divinylbenzene (81.4%) and 5.88 g of dibenzoyl peroxide was added. To remove atmospheric oxygen, the mixture was then sparged with nitrogen for 15 minutes. Subsequently, the reactor contents were brought to 30° C. within 30 minutes and kept at this temperature for 30 minutes. A solution of 3.2 g of methylhydroxyethylcellulose dissolved in 157 g of water was then added, and the mixture was stirred at 30° C. for another 1 hour. The mixture was heated to 62° C. for 16 hours. Then 30 g of diethylene glycol divinyl ether and a solution of 5 g of potassium peroxodisulfate in 50 ml of water were added at 62° C. in two separate feeds within 30 minutes. The mixture was then heated to 95° C. for 2 hours. After cooling, the mixture was washed over a 315 μm screen and dried. 1539 g of a monodisperse bead polymer having a mean particle size of 448 μm were obtained.

2b) Production of a Cation Exchanger

The procedure was as in example C3b), except that 700 g of bead polymer from 2a) were introduced and the mixture was stirred at 115° C. for 10 hours instead of at 105° C. for 5 hours.

3920 ml of monodisperse cation exchanger in the H form with a total capacity, based on the H form, of 2.12 eq/l were obtained.

Example 3

(Inventive)

3a) Preparation of Bead Polymers with Diethylene Glycol Divinyl Ether

In a 4 l stirred reactor with gate stirrer, condenser, temperature sensor and thermostat and temperature recorder, an aqueous initial charge composed of 1443 g of deionized water, 4.85 g of boric acid and 2.72 g of 50% by weight sodium hydroxide solution was obtained. To this initial charge were added, with stirring at 200 rpm, 864.9 g of seed polymer prepared as in example 1.

Within 30 min, a mixture of S g of styrene (see table), 109.5 g of divinylbenzene (81.3%), X g of diethylene glycol divinyl ether (DEGDVE, see table) and 2.35 g of tert-butyl peroxy-2-ethylhexanoate was added. To remove atmospheric oxygen, the mixture was then sparged with nitrogen for 15 minutes. Subsequently, the reactor contents were brought to 30° C. within 30 minutes and kept at this temperature for 30 minutes. Then a solution of 3.2 g of methylhydroxyethylcellulose dissolved in 157 g of water was added and the mixture was stirred at 30° C. for another hour. The mixture was heated to 65° C. for 11 hours and then to 95° C. for 2 hours. After cooling, the mixture was washed over a 315 μm screen and dried. Y g of a monodisperse bead polymer were obtained (see table).

3b) Production of Cation Exchangers

The procedure was as in example C2b), except that in each case 350 g of bead polymer from 3a) were introduced.

Z ml of monodisperse cation exchanger in the H form with a total capacity, based on the H form, of TC eq/l were obtained (see Tab. 1).

TABLE 1

| Example | Amount S of styrene | Amount X of DEGDVE | Yield Y of polymer | Yield Z of resin | TC of the resin |
|---|---|---|---|---|---|
| 3.1 | 618.3 g | 7.4 g | 1575 g | 1400 ml | 2.20 eq/l |
| 3.2 | 603.5 g | 22.2 g | 1574 g | 1400 ml | 2.18 eq/l |
| 3.3 | 588.7 g | 37.0 g | 1580 g | 1380 ml | 2.17 eq/l |

Example 4

(Inventive)

4a) Preparation of a Bead Polymer with Butanediol Divinyl Ether

The procedure was as in example 2a), except that 30 g of butanediol divinyl ether were used instead of 30 g of ethylene glycol divinyl ether.

1550 g of a monodisperse bead polymer were obtained.

4b) Production of a Cation Exchanger

A 4 l stirred reactor with gate stirrer, temperature sensor, distillation system and thermostat and temperature recorder was initially charged with 1200 ml of 98% by weight sulfuric acid and heated to 100° C. Within 30 minutes, 300 g of bead polymer from 4a) were introduced in 10 portions with stirring. Subsequently, the mixture was stirred at 115° C. for 5 hours and at 135° C. for 2 hours. After cooling, the suspension was transferred into a glass column. Sulfuric acid of decreasing concentration, beginning with 90% by weight and ending with pure water, was applied to the column from the top.

1280 ml of monodisperse cation exchanger in the H form with a total capacity, based on the H form, of 2.19 eq/l were obtained.

Example 5

(Inventive)

5a) Preparation of a Bead Polymer with Ethylene Glycol Monovinyl Ether

The procedure was as in example 2a), except using 30 g of ethylene glycol monovinyl ether instead of 30 g of ethylene glycol divinyl ether.

1670 g of a monodisperse bead polymer were obtained.

5b) Production of a Cation Exchanger

The procedure was as in example 4b), except that 1400 ml of 98% by weight sulfuric acid were initially charged and 350 g of bead polymer from 5a) were introduced.

1470 ml of monodisperse cation exchanger in the H form with a total capacity, based on the H form, of 2.21 eq/l were obtained.

Example 6

(Inventive)

6a) Preparation of a Bead Polymer with Vinyl Acetate

The procedure was as in example 2a), except that 30 g of vinyl acetate were used instead of 30 g of ethylene glycol divinyl ether.

1264 g of a monodisperse bead polymer were obtained.

6b) Production of a Cation Exchanger

The procedure was as in example 5b with 350 g of bead polymer from 6a).

1480 ml of monodisperse cation exchanger in the H form with a total capacity, based on the H form, of 2.17 eq/l were obtained.

Example 7

(Inventive)

7a) Preparation of a Bead Polymer with Diethylene Glycol Divinyl Ether

Example 2a was repeated. 1570 g of a monodisperse bead polymer were obtained.

7b) Production of a Cation Exchanger

The procedure was analogous to comparative example C1b), except that 664 ml of 84.7% by weight sulfuric acid were initially charged at room temperature and 350 g of bead polymer from 7a) were used and 227 ml of oleum were added.

1500 ml of monodisperse cation exchanger in the H form with a total capacity, based on the H form, of 2.08 eq/l were obtained.

Example 8

(Inventive)

8a) Preparation of a Bead Polymer with Diethylene Glycol Divinyl Ether

In a 4 l stirred reactor with gate stirrer, condenser, temperature sensor and thermostat and temperature recorder, an aqueous initial charge composed of 1400 g of deionized water, an aqueous initial charge composed of 1400 g of deionized water, 6.88 g of disodium hydrogenphosphate dodecahydrate and 90.3 g of a 2% aqueous solution of methylhydroxyethylcellulose was obtained.

Thereafter, a mixture of 1316.4 g of styrene, 137.7 g of divinylbenzene (80.3%), 14.7 g of diethylene glycol divinyl ether and 11.8 g of dibenzoyl peroxide (75% by weight in water) was added. The reactor contents were left to stand at room temperature for 30 minutes, in the course of which two phases formed. Then the stirrer was switched on at 180 rpm and the mixture was stirred at room temperature for 30 minutes. The reactor contents were subsequently heated at 62° C. for 16 hours and at 95° C. for 2 hours. After cooling, the mixture was washed over a 315 µm screen and dried. 1441 g of a heterodisperse bead polymer were obtained.

8b) Production of a Cation Exchanger

The procedure was analogous to comparative example C1b), except that 1110 ml of 86% by weight sulfuric acid were initially charged at room temperature, 350 g of bead polymer from 8a) were used and 322 ml of oleum were added. The mixture was stirred only at 115° C. for 5 hours (without the 140° C. stage).

1590 ml of heterodisperse cation exchanger in the H form with a total capacity, based on the H form, of 1.90 eq/l were obtained.

Example 9

(Inventive)

9a) Preparation of a Macroporous Bead Polymer with Diethylene Glycol Divinyl Ether In a 4 l stirred reactor with gate stirrer, condenser, temperature sensor and thermostat and temperature recorder, an aqueous initial charge composed of 1112 g of deionized water, 7.86 g of disodium hydrogenphosphate dodecahydrate and 149 g of a 2.2% aqueous solution of methylhydroxyethylcellulose was obtained.

Thereafter, a mixture of 812 g of styrene, 140.2 g of divinylbenzene (81.8%), 19.1 g of diethylene glycol divinyl ether, 421 g of isododecane and 5.73 g of tert-butyl peroxy-2-ethylhexanoate was added. The reactor contents were left to stand at room temperature for 20 minutes, in the course of which two phases formed. Then the stirrer was switched on at 300 rpm and the mixture was stirred at room temperature for 30 minutes. The reactor contents were then stirred at 70° C. for 7 hours and at 95° C. for 2 hours. After cooling, the mixture was washed over a 315 µm screen and dried. 959 g of a macroporous, heterodisperse bead polymer were obtained (r=revolutions).

9b) Production of a Macroporous Cation Exchanger

The procedure was analogous to comparative example C2b), except that 350 g of bead polymer from 9a) were introduced into the sulfuric acid at 115° C. (instead of at 100° C.).

1600 ml of heterodisperse cation exchanger in the H form with a total capacity, based on the H form, of 1.90 eq/l were obtained.

Comparative Example 4

(Noninventive)

C4a) Preparation of a Macroporous Bead Polymer without Comonomer

The procedure was as in example 9a), except that the diethylene glycol divinyl ether was omitted. 936 g of a macroporous, heterodisperse bead polymer were obtained.

C4b) Production of a Macroporous Cation Exchanger

The procedure was as in example 9b), except that 350 g of bead polymer from C4a) were introduced into the sulfuric acid at 115° C.

1640 ml of heterodisperse cation exchanger in the H form with a total capacity, based on the H form, of 1.87 eq/l were obtained.

TABLE 2

Test results for osmotic and oxidation stability of examples 2 to 9 and of comparative examples 1 to 4

| Example | TC (eq/l) | OS | SS | Reddening test after 4 weeks | | |
|---|---|---|---|---|---|---|
| | | | | pH | Abs. 225 nm | Mark |
| C1 | 2.08 | 90 | 84 | 3.33 | 2.91 | 1 |
| C2 | 2.20 | 97 | n.d. | 3.38 | 2.10 | 2 |
| C3 | 1.92 | 97 | 89 | 2.79 | >4 | 3 |
| C4 | 1.87 | 100 | n.d. | 3.46 | 2.57 | 2 |
| 2 | 2.12 | 95 | 93 | 3.64 | 0.59 | 1 |
| 3.1 | 2.20 | 94 | 92 | 3.55 | 1.19 | 1 |
| 3.2 | 2.18 | 98 | 91 | 3.50 | 0.95 | 1 |
| 3.3 | 2.17 | 96 | 95 | 3.62 | 0.61 | 0 |
| 4 | 2.19 | 97 | 97 | 3.57 | 0.61 | 1 |
| 5 | 2.21 | 99 | 96 | 3.54 | 1.22 | 1 |

TABLE 2-continued

Test results for osmotic and oxidation stability of examples 2 to 9 and of comparative examples 1 to 4

| | | | | | Reddening test after 4 weeks | |
|---|---|---|---|---|---|---|
| Example | TC (eq/l) | OS | SS | pH | Abs. 225 nm | Mark |
| 6 | 2.17 | 98 | 90 | 3.54 | 1.04 | 2 |
| 7 | 2.08 | 99 | 85 | 3.58 | 0.70 | 1 |
| 8 | 1.90 | 95 | n.d. | 3.56 | 2.00 | 2 |
| 9 | 1.90 | 100 | n.d. | 3.61 | 1.64 | 3 |

TC = total capacity;
OS = original stability;
SS = swelling stability

Example 10

Determination of the Oxidation Stability of the Resins

The resins from examples 2 to 8 and from comparative examples C1 to C3 were subjected to the reddening test.

The pH gives information as to how much soluble acid (principally polystyrenesulfonic acid, so-called leaching, combined with small amounts of sulfuric acid from the hydrolysis of the sulfonic acid groups of the resin) has been formed under air after a given storage time; the absorption at 225 nm is a measure for the water-soluble aromatic compounds released, in this case oligomeric and polymeric styrenesulfonic acids.

In the test:
the higher the pH of the eluate, the smaller the amount of soluble acid which has been released by the resin, and the higher the oxidation stability of the resins;
the lower the absorption value of the eluate at 225 nm, the smaller the amount of soluble aromatic compounds which has been released by the resin, and the higher the oxidation stability of the resins;
the lower the mark in the visual assessment of the eluate, the more colorless the eluate.

The results of the osmotic stability and of the oxidation stability test for the different examples and comparative examples are reported in Tab. 2.

Tab. 2 shows that the inventive strongly acidic cation exchangers possess total capacities which are in no way inferior to the total capacity of the comparative examples.

It can be seen that the inventive strongly acidic cation exchangers have very high original and swelling stability values which are comparable to or higher than the values of the comparative examples corresponding to the state of the art.

All inventive cationic exchangers have, in the reddening test, a higher pH of the eluate and a lower absorption value of the eluate at 225 nm than the comparative examples. This demonstrates a significantly reduced release of soluble polystyrenesulfonic acids from the inventive resins and hence the higher oxidation stability of the inventive resins.

Tab. 2 also shows that the improvement in the profile of properties of the inventive strongly acidic cation exchangers is particularly marked for the divinyl ether compounds (examples 2, 3, 4, 7).

Comparison of examples 2, 3 and 4 shows that the effect of adding vinyl ether and/or vinyl ester in the polymerization is independent of the type and of the time of comonomer incorporation.

Example 9 compared with comparative example 4 reveals that the improvement in the oxidation stability of the strongly acidic cation exchangers as a result of the inventive incorporation of vinyl ether(s) and/or vinyl ester(s) also occurs in the case of macroporous resins.

What is claimed is:

1. Strongly acidic cation exchangers obtained by reacting:
a vinylaromatic monomer,
a crosslinker, and
from 0.2 to 20 percent by weight of a divinyl ether, thereby forming bead polymers,
wherein the bead polymers are prepared by a seed-feed process employing a crosslinked seed polymer; and
subsequently sulfonating said bead polymers,
wherein the strongly acidic cation exchangers have a reddening mark of less than 2.

2. The strongly acidic cation exchangers according to claim 1, wherein the vinylaromatic monomer comprises at least one monoethylenically unsaturated aromatic monomer, and
wherein the divinyl ether is selected from the group consisting of ethylene glycol divinyl ether, diethylene glycol divinyl ether, and butanediol divinyl ether.

3. The strongly acidic cation exchangers as claimed in claim 1 having a monodisperse particle size distribution.

4. The strongly acidic cation exchangers as claimed in claim 1 having a macroporous structure.

5. A process for producing strongly acidic cation exchangers, comprising:
a) suspension polymerization of a vinylaromatic monomer, a crosslinker, and from 0.2 to 20% by weight of a divinyl ether, thereby forming bead polymers, wherein said suspension polymerization is via a seed-feed process employing a crosslinked seed polymer; and
b) reacting said bead polymers with sulfuric acid, sulfur trioxide and/or chlorosulfonic acid, thereby forming the strongly acidic cation exchangers, and
wherein the strongly acidic cation exchangers have a reddening mark of less than 2.

6. The method according to claim 5, wherein said liquid is water and wherein the divinyl ether is selected from the group consisting of ethylene glycol divinyl ether, diethylene glycol divinyl ether, and butanediol divinyl ether.

7. A method for removing substances from a liquid having removable substances contained therein, comprising:
contacting the liquid with the strongly acidic cation exchangers according to claim 1.

8. A method for chromatographically separating glucose and fructose, comprising:
contacting the glucose and the fructose with the strongly acidic cation exchangers according to claim 1.

9. A method of catalyzing a chemical reaction, comprising:
performing the chemical reaction in the presence of the strongly acidic cation exchangers according to claim 1.

10. The method according to claim 9, wherein the chemical reaction is the production of bisphenol A from phenol and acetone.

* * * * *